US010522249B2

(12) United States Patent
Park et al.

(10) Patent No.: US 10,522,249 B2
(45) Date of Patent: Dec. 31, 2019

(54) MULTIPLE COMPUTER SERVER SYSTEM FOR ORGANIZING HEALTHCARE INFORMATION

(71) Applicant: BIOPOLICY INNOVATIONS INC., Vancouver, BC (CA)

(72) Inventors: Andrew Park, Blaine, WA (US); Drew Gutschmidt, Vancouver (CA)

(73) Assignee: Biopolicy Innovations Inc., Vancouver, BC (CA)

( * ) Notice: Subject to any disclaimer, the term of this patent is extended or adjusted under 35 U.S.C. 154(b) by 398 days.

(21) Appl. No.: 14/831,701

(22) Filed: Aug. 20, 2015

(65) Prior Publication Data

US 2015/0356259 A1    Dec. 10, 2015

Related U.S. Application Data

(63) Continuation-in-part of application No. 14/265,118, filed on Apr. 29, 2014.

(30) Foreign Application Priority Data

Apr. 29, 2013  (CA) ..................................... 2814365

(51) Int. Cl.
*G16H 40/20* (2018.01)
*G06Q 40/08* (2012.01)
*G06Q 50/22* (2018.01)
*G06F 19/00* (2018.01)

(52) U.S. Cl.
CPC .......... *G16H 40/20* (2018.01); *G06F 19/328* (2013.01); *G06Q 40/08* (2013.01); *G06Q 50/22* (2013.01); *G06F 19/324* (2013.01)

(58) Field of Classification Search
CPC ........ G06Q 50/22; G06Q 50/24; G06Q 40/08; G06F 19/328; G06F 19/324; G16H 40/20
USPC .......................................................... 705/2–3
See application file for complete search history.

(56) References Cited

U.S. PATENT DOCUMENTS

| | | | |
|---|---|---|---|
| 7,860,735 B2 | 12/2010 | Evanitsky | |
| 8,218,887 B2 | 7/2012 | Zyuzin | |
| 8,364,688 B1 * | 1/2013 | Thomas | G06Q 10/10 |
| | | | 707/758 |
| 9,311,399 B2 * | 4/2016 | Thomas | G06F 16/95 |
| 2002/0120776 A1 | 8/2002 | Eggebraaten et al. | |
| 2003/0219709 A1 | 11/2003 | Olenick et al. | |
| 2003/0233278 A1 | 12/2003 | Marshall | |
| 2005/0187948 A1 | 8/2005 | Monitzer et al. | |

(Continued)

*Primary Examiner* — Joy Chng (74) *Attorney, Agent, or Firm* — Stites & Harbison PLLC; Jeffrey A. Haeberlin (57) ABSTRACT

A method of providing changes in healthcare policy information is provided, including: providing a first database, the first database containing a plurality of records, each record containing a copy of a website and tags associated with the website, the website pertaining to healthcare policy information; retrieving current versions of tags associated with the websites on the Internet; for each website, determining if the tags associated with the website have changed by comparing the current version of the tags to the copy of the tags in the first database; if the tags have changed, updating the copy of the website associated with the tags in the first database; determining the changes in the website, and providing access to reports generated to reflect changes in the website.

7 Claims, 10 Drawing Sheets

(56) References Cited

U.S. PATENT DOCUMENTS

| | | |
|---|---|---|
| 2006/0293923 A1 | 12/2006 | Farris |
| 2008/0059224 A1 | 3/2008 | Schechter |
| 2008/0177994 A1* | 7/2008 | Mayer .................. G06F 9/4418 713/2 |
| 2008/0221936 A1 | 9/2008 | Patterson |
| 2011/0112873 A1 | 5/2011 | Allen et al. |
| 2012/0078651 A1 | 3/2012 | Henderson et al. |
| 2013/0283147 A1* | 10/2013 | Wong ..................... G06F 17/21 715/234 |
| 2013/0290270 A1 | 10/2013 | Pareek |
| 2014/0142989 A1 | 5/2014 | Grosso |

* cited by examiner

Search Page for Data Report

Master

Therapy

Therapy Category

Therapy Subcategory

Select Policies to Compare

Select All

Cervarix
Gardasil

Select Payer (s)

Cigna
Humana
Payer 3
Payer 4

Select Data Points

Coverage

Formulary Tier

Coding

Review Date

Quantity Limit

Step-Therapy

Co-Pay

Additional User-Defined Comparable Fields

Plan Name

Covered Lives

Create Report

FIG. 5a

Output from 5a

[Report Results]

| | Cigna | Humana | Payer 3 | Payer 4 |
|---|---|---|---|---|
| Coverage | Yes | | Yes | Yes |
| Next Review Date | 2013-10-15 | | 2014-02-03 | 2013-06-28 |
| Formulating Tier | --- | | 4 | 5 |
| Coding | 90649<br>V04.89 | --- | 90649<br>90650 | V03.6<br>V02.8<br>V69.2 |
| Policy | Gardasil | --- | Gardasil | Gardasil |
| Additional User-Defined Comparable Fields | --- | --- | --- | --- |

MULTIPLE COMPUTER SERVER SYSTEM FOR ORGANIZING HEALTHCARE INFORMATION

RELATED APPLICATIONS

This application is a continuation-in-part of U.S. patent application Ser. No. 14/265,118 filed on Apr. 29, 2014, which is hereby incorporated by reference in its entirety.

FIELD OF THE INVENTION

The present invention relates to detecting and organizing changes in policies, and more specifically to healthcare policies.

BACKGROUND

A medical manufacturing company that provides pharmaceuticals or medical devices will naturally be interested in which insurance companies provide coverage for its products, as the more insurance companies that provide coverage for the product, the larger the potential customer base. Healthcare professionals, such as medical manufacturing companies, currently rely on a cumbersome manual system of determining if healthcare insurance policies have been updated or changed. However, most healthcare professionals find out about changes to an insurer's coverage policies passively through newsletters and the like, or anecdotally through others in the industry, long after the change has occurred.

The predominant method of keeping track of insurer healthcare updates is to subscribe to newsletters and manually visit websites to see if a change has occurred. This is not an adequate solution due to the time required to visit the voluminous number of websites that carry relevant information and the human error that can miss a change (assuming such a change occurred on the website accessed). Subscribing to newsletters is also inadequate because health insurers do not always update their newsletters comprehensively, nor release them on a regular schedule; and newsletters are frequently released long after a change has actually occurred. It is thus important for stakeholders to find out about a change in policy as quickly as possible after it occurs.

Generic software crawling technology is available, but is not targeted specifically towards the healthcare industry and the needs of medical device manufacturers, pharmaceutical manufacturers, diagnostic companies, dental device manufacturers, professional healthcare associations and insurance companies; and offers no organization of the information once a change is detected.

A proposed solution exists that offers a query based database that contains names of health plans of tiers of pharmaceuticals, but fails to offer a database of update notifications and does not include information on medical devices; only pharmaceuticals.

Another proposed solution offers an alert service for healthcare policy websites, but does not provide an analytical database that can customize, target and sort information within a policy or policy change, including information such as prior authorization requirements and current procedural terminology coding, and fails to provide a corresponding analytical tool.

Other services provide a similar function but lack a targeted organized database of information that can be accessed via multiple searches and targeted data queries and are unable to produce customized reports that are updated along with the changes produced by a computer system.

Another proposed solution is found in U.S. Patent Application Publication No. 2011/0112873 disclosing a system and method for electronically monitoring, alerting and evaluating changes in a health care payor policy.

SUMMARY OF THE INVENTION

The system according to the invention scans a large volume of information available in a database of downloaded websites and documents, which are available through the Internet, to detect targeted changes related to healthcare insurance policies, using criteria selectable by a user. The information is then condensed to a format that is easily ported into a second database that houses and organizes the new information. The second database is accessible by the user and drop down menus are available to allow the user to generate a report displaying selected elements of healthcare policies in rows, with the name of the insurer in the column headings. The system according to the invention can use multiple servers to scan websites to collect and process large volumes of information.

The system can allow stacking of servers, so all servers contribute to the singular data output produced by the main server. Each server can act independently of the others so disruption to a single server does not affect any processes or jobs of other servers.

The system and method according to the invention solves the problem of scanning a huge web domain of information that could not be done completely in a manual fashion, multiple times a day. With the system, any changes to healthcare policies are detected no less than 24 hours after being posted on the web. A user interface that sorts the information allows ease of use and readability. By porting the information into a second database where it is organized and queried with a user-driven analytical tool, users gain additional insight into each policy and can compare consistent features of each policy across multiple insurance payers. This automated database provides the payer names as the columns, under which are healthcare policy specific data components (such as therapy coverage, prior authorization, previous and next review dates, coding).

Multiple computer servers can be used to detect changes in a database of policies relevant to each user and to continually scan the websites in which the policies are located to download the policies into the database and capture the changes, which undergo further processing before the information is presented to the user.

The system allows users to receive change updates to their policies of interest, without having to continually and manually log into each insurer's website and determine if there is a change. The system has the ability to capture insurance policy information from insurers and health technology assessments in the US, Europe, Latin America, Canada and other countries around the world.

The system is designed to specifically target predefined medical therapies in a designated database of websites for easy software based manipulation of change data.

The system creates value for the user as the user can pick out changes to a volume of documentation that is impossible to scan efficiently through human effort alone. The system also removes the element of human error when determining if a document has changed. The user enjoys the benefit of having change information delivered to them much quicker than passively waiting for inconsistent and unreliable newsletter announcements from insurers (every insurer has disparate procedures in releasing newsletters, and many do not release them at all). Additional value is offered in a second database that houses much of the change information in a format that allows querying of specific data within policies, allowing the user to produce a report comparing this data across multiple insurers of their choosing.

The system can alert the user to changes in documentation automatically via email, Short Message Service (SMS) or mobile application push notifications, thereby allowing the user to keep apprised of changes daily.

A method of providing changes in healthcare policy information is provided, including: providing a first database, the first database containing a plurality of records, each record containing a copy of a website, the website pertaining to healthcare policy information; scanning current versions of the websites on the Internet and determining which of the websites have changed by comparing the current version of the website on the Internet to the copy in the first database; then identifying the website to a first server; and updating the copy of the website in the first database; and providing access to reports generated to reflect changes in the website.

The first server may determine the changes made to each of the websites identified by a second server that scans the current versions of the websites. Records including the changes made to each of the websites identified by the second server may be stored in a second database. A first user interface may allow a user to search the first database. The second database may be searchable by the user through a second user interface.

A field of each record in the first database may include at least one of the fields selected from the following: procedure name, medical device name, diagnostic test name, guideline name, vaccine name, drug name; name of insurer; and health plan name. A field of each record in the second database may include at least one of the fields selected from the following: procedure name, medical device name, diagnostic test name, guideline name, vaccine name, website name; insurer name; and coverage criteria.

A system for managing healthcare policy information is provided, including: a first database, the first database containing records including copies of websites, the websites pertaining to policy information; a first server configured to scan current versions of the websites on the Internet and identifying which of the current websites have been changed since a previous scan of the website to a second server; and updating the records in the first database; and a second server configured to generate a report of the changes made to each of the identified websites; the second server also configured to provide access to a user to generate reports relating to the websites.

The second server may be configured to determine the changes made to the websites identified by the first server and to generate an alert for a user on a change to a preselected website, the alert including information about the change to the preselected website. The system may include a mobile device application connected to the first database and the second database thereby allowing users to access and interact with healthcare policy data stored on the first and second databases.

A system for viewing healthcare policy information is provided, including: a database containing a plurality of websites, the websites corresponding to copies of websites pertaining to healthcare insurance coverage policies; a second database of user selectable data fields containing elements of websites stored in the first database; a user interface whereby a user can view and download healthcare insurance coverage information related to the healthcare insurance coverage policies, the policies sortable by procedure name, medical device name, diagnostic test name, guideline name, vaccine name, website name; insurer name; and coverage criteria; a server in communication with the first and second databases, the server configured to generate data output from criteria selectable by the user through interactive menus; and means for exporting the data output into a selected data formats.

A method of providing changes in healthcare policy information is provided, including: providing a first database, the first database containing a plurality of records, each record containing a copy of a website and tags associated with the website, the website pertaining to healthcare policy information; retrieving current versions of tags associated with the websites on the Internet; for each website, determining if the tags associated with the website have changed by comparing the current version of the tags to the copy of the tags in the first database; if the tags have changed, updating the copy of the website associated with the tags in the first database; determining the changes in the website, and providing access to reports generated to reflect changes in the website. One or more servers may simultaneously retrieve the tags associated with the plurality of websites.

A system for providing changes in healthcare policy information is provided, including: a first database, the first database containing a plurality of records, each record containing a copy of a website and tags associated with the website, the website pertaining to healthcare policy information; a computer configured to request a plurality of servers to simultaneously retrieve current versions of tags associated with the websites on the Internet; the computer further configured to, for each website, determine if the tags associated with the website have changed by comparing the current version of the tags to the copy of the tags in the first database; and if the tags have changed, updating the copy of the website associated with the tags in the first database; determining the changes in the website, and providing access to reports generated to reflect changes in the website.

DETAILED DESCRIPTION OF THE INVENTION

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

The methods and displays with the applications described herein are not inherently related to any particular computing device or other apparatus. Various general-purpose systems may be used with programs in accordance with the teachings herein, or it may prove convenient to construct more specialized apparatus to perform the required machine-implemented method operations. The required structure for a variety of these systems will appear from the description below. In addition, embodiments of the present invention are not described with reference to any particular programming language. It will be appreciated that a variety of programming languages may be used to implement the teachings of embodiments of the invention as described herein.

An embodiment of the invention may be implemented as a method or as a machine readable non-transitory storage medium that stores executable instructions that, when executed by a data processing system, causes the system to perform a method. An apparatus, such as a data processing system, can also be an embodiment of the invention. Other features of the present invention will be apparent from the accompanying drawings and from the detailed description which follows.

Terms

The term "invention" and the like mean "the one or more inventions disclosed in this application", unless expressly specified otherwise.

The terms "an aspect", "an embodiment", "embodiment", "embodiments", "the embodiment", "the embodiments", "one or more embodiments", "some embodiments", "certain embodiments", "one embodiment", "alternate embodiment", "another embodiment" and the like mean "one or more (but not all) embodiments of the disclosed invention(s)", unless expressly specified otherwise.

A reference to "another embodiment", "alternative" embodiment", "alternate embodiment" or "another aspect" in describing an embodiment does not imply that the referenced embodiment is mutually exclusive with another embodiment (e.g., an embodiment described before the referenced embodiment), unless expressly specified otherwise.

The terms "including", "comprising" and variations thereof mean "including but not limited to", unless expressly specified otherwise.

The terms "a", "an" and "the" mean "one or more", unless expressly specified otherwise. The term "plurality" means "two or more", unless expressly specified otherwise. The term "herein" means "in the present application, including anything which may be incorporated by reference", unless expressly specified otherwise.

The term "e.g." and like terms mean "for example", and thus does not limit the term or phrase it explains. For example, in a sentence "the computer sends data (e.g., instructions, a data structure) over the Internet", the term "e.g." explains that "instructions" are an example of "data" that the computer may send over the Internet, and also explains that "a data structure" is an example of "data" that the computer may send over the Internet. However, both "instructions" and "a data structure" are merely examples of "data", and other things besides "instructions" and "a data structure" can be "data".

The term "respective" and like terms mean "taken individually". Thus if two or more things have "respective" characteristics, then each such thing has its own characteristic, and these characteristics can be different from each other but need not be. For example, the phrase "each of two machines has a respective function" means that the first such machine has a function and the second such machine has a function as well. The function of the first machine may or may not be the same as the function of the second machine.

Where two or more terms or phrases are synonymous (e.g., because of an explicit statement that the terms or phrases are synonymous), instances of one such term/phrase does not mean instances of another such term/phrase must have a different meaning. For example, where a statement renders the meaning of "including" to be synonymous with "including but not limited to", the mere usage of the phrase "including but not limited to" does not mean that the term "including" means something other than "including but not limited to".

Neither the Title (set forth at the beginning of the first page of the present application) nor the Abstract (set forth at the end of the present application) is to be taken as limiting in any way as the scope of the disclosed invention(s). An Abstract has been included in this application merely because an Abstract of not more than 150 words is required under 37 C.F.R. section 1.72(b). The title of the present application and headings of sections provided in the present application are for convenience only, and are not to be taken as limiting the disclosure in any way.

Numerous embodiments are described in the present application, and are presented for illustrative purposes only. The described embodiments are not, and are not intended to be, limiting in any sense. The presently disclosed invention (s) are widely applicable to numerous embodiments, as is readily apparent from the disclosure. One of ordinary skill in the art will recognize that the disclosed invention(s) may be practiced with various modifications and alterations, such as structural and logical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

No embodiment of method steps or product elements described in the present application constitutes the invention claimed herein, or is essential to the invention claimed herein, or is coextensive with the invention claimed herein, except where it is either expressly stated to be so in this specification or expressly recited in a claim.

The invention can be implemented in numerous ways, including as a process, an apparatus, a system, a computer readable medium such as a computer readable storage medium or a computer network wherein program instructions are sent over optical or communication links. In this specification, these implementations, or any other form that the invention may take, may be referred to as systems or techniques. A component such as a processor or a memory described as being configured to perform a task includes both a general component that is temporarily configured to perform the task at a given time or a specific component that is manufactured to perform the task. In general, the order of the steps of disclosed processes may be altered within the scope of the invention.

The following discussion provides a brief and general description of a suitable computing environment in which various embodiments of the system may be implemented. Although not required, embodiments will be described in the general context of computer-executable instructions, such as program applications, modules, objects or macros being executed by a computer. Those skilled in the relevant art will appreciate that the invention can be practiced with other computer configurations, including mobile computing devices, such as smart phones, tablets and phablets, multi-processor systems, microprocessor-based or programmable consumer electronics, personal computers ("PCs"), network PCs, mini-computers, mainframe computers, and the like. The embodiments can be practiced in distributed computing environments where tasks or modules are performed by remote processing devices, which are linked through a communications network. In a distributed computing environment, program modules may be located in both local and remote memory storage devices.

A computer system may be used as a server including one or more processing units, system memories, and system buses that couple various system components including system memory to a processing unit. Computers, such as mobile computing devices, will at times be referred to in the singular herein, but this is not intended to limit the application to a single computing system since in typical embodiments, there will be more than one computing system or other device involved. Other computer systems may be employed, such as conventional and personal computers, where the size or scale of the system allows. The processing unit may be any logic processing unit, such as one or more central processing units ("CPUs"), digital signal processors ("DSPs"), application-specific integrated circuits ("ASICs"), etc. Unless described otherwise, the construction and operation of the various components are of conventional design. As a result, such components need not be described in further detail herein, as they will be understood by those skilled in the relevant art.

A computer system includes a bus, and can employ any known bus structures or architectures, including a memory bus with memory controller, a peripheral bus, and a local bus. The computer system memory may include read-only memory ("ROM") and random access memory ("RAM"). A basic input/output system ("BIOS"), which can form part of the ROM, contains basic routines that help transfer information between elements within the computing system, such as during startup.

A computer system also includes non-volatile memory. The non-volatile memory may take a variety of forms, for example a hard disk drive for reading from and writing to a hard disk, and an optical disk drive and a magnetic disk drive for reading from and writing to removable optical disks and magnetic disks, respectively. The optical disk can be a CD-ROM, while the magnetic disk can be a magnetic floppy disk or diskette. The hard disk drive, optical disk drive and magnetic disk drive communicate with the processing unit via the system bus. The hard disk drive, optical disk drive and magnetic disk drive may include appropriate interfaces or controllers coupled between such drives and the system bus, as is known by those skilled in the relevant art. The drives, and their associated computer-readable media, provide non-volatile storage of computer readable instructions, data structures, program modules and other data for the computing system. Although a computing system may employ hard disks, optical disks and/or magnetic disks, those skilled in the relevant art will appreciate that other types of non-volatile computer-readable media that can store data accessible by a computer system may be employed, such a magnetic cassettes, flash memory cards, digital video disks ("DVD"), Bernoulli cartridges, RAMs, ROMs, smart cards, etc.

Various program modules or application programs and/or data can be stored in the computer memory. For example, the system memory may store an operating system, end user application interfaces, server applications, and one or more application program interfaces ("APIs").

The computer system memory also includes one or more networking applications, for example a Web server application and/or Web client or browser application for permitting the computer to exchange data with sources via the Internet, corporate Intranets, or other networks as described below, as well as with other server applications on server computers such as those further discussed below. The networking application in the preferred embodiment is markup language based, such as hypertext markup language ("HTML"), extensible markup language ("XML") or wireless markup language ("WML"), and operates with markup languages that use syntactically delimited characters added to the data of a document to represent the structure of the document. A number of Web server applications and Web client or browser applications are commercially available, such those available from Mozilla and Microsoft. The operating system and various applications/modules and/or data can be stored on the hard disk of the hard disk drive, the optical disk of the optical disk drive and/or the magnetic disk of the magnetic disk drive.

A computer system can operate in a networked environment using logical connections to one or more client computers and/or one or more database systems, such as one or more remote computers or networks. A computer may be logically connected to one or more client computers and/or database systems under any known method of permitting computers to communicate, for example through a network such as a local area network ("LAN") and/or a wide area network ("WAN") including, for example, the Internet. Such networking environments are well known including wired and wireless enterprise-wide computer networks, intranets, extranets, and the Internet. Other embodiments include other types of communication networks such as telecommunications networks, cellular networks, paging networks, and other mobile networks. The information sent or received via the communications channel may, or may not be encrypted. When used in a LAN networking environment, a computer is connected to the LAN through an adapter or network interface card (communicatively linked to the system bus). When used in a WAN networking environment, a computer may include an interface and modem or other device, such as a network interface card, for establishing communications over the WAN/Internet.

In a networked environment, program modules, application programs, or data, or portions thereof, can be stored in a computer for provision to the networked computers. In one embodiment, the computer is communicatively linked through a network with TCP/IP middle layer network protocols; however, other similar network protocol layers are used in other embodiments, such as user datagram protocol ("UDP"). Those skilled in the relevant art will readily recognize that these network connections are only some examples of establishing communications links between computers, and other links may be used, including wireless links. While in most instances a computer will operate automatically, where an end user application interface is provided, a user can enter commands and information into the computer through a user application interface including input devices, such as a keyboard, and a pointing device, such as a mouse. Other input devices can include a microphone, joystick, scanner, etc. These and other input devices are connected to the processing unit through the user application interface, such as a serial port interface that couples to the system bus, although other interfaces, such as a parallel port, a game port, or a wireless interface, or a universal serial bus ("USB") can be used. A monitor or other display device is coupled to the bus via a video interface, such as a video adapter. The computer can include other output devices, such as speakers, printers, etc.

Figure 1:
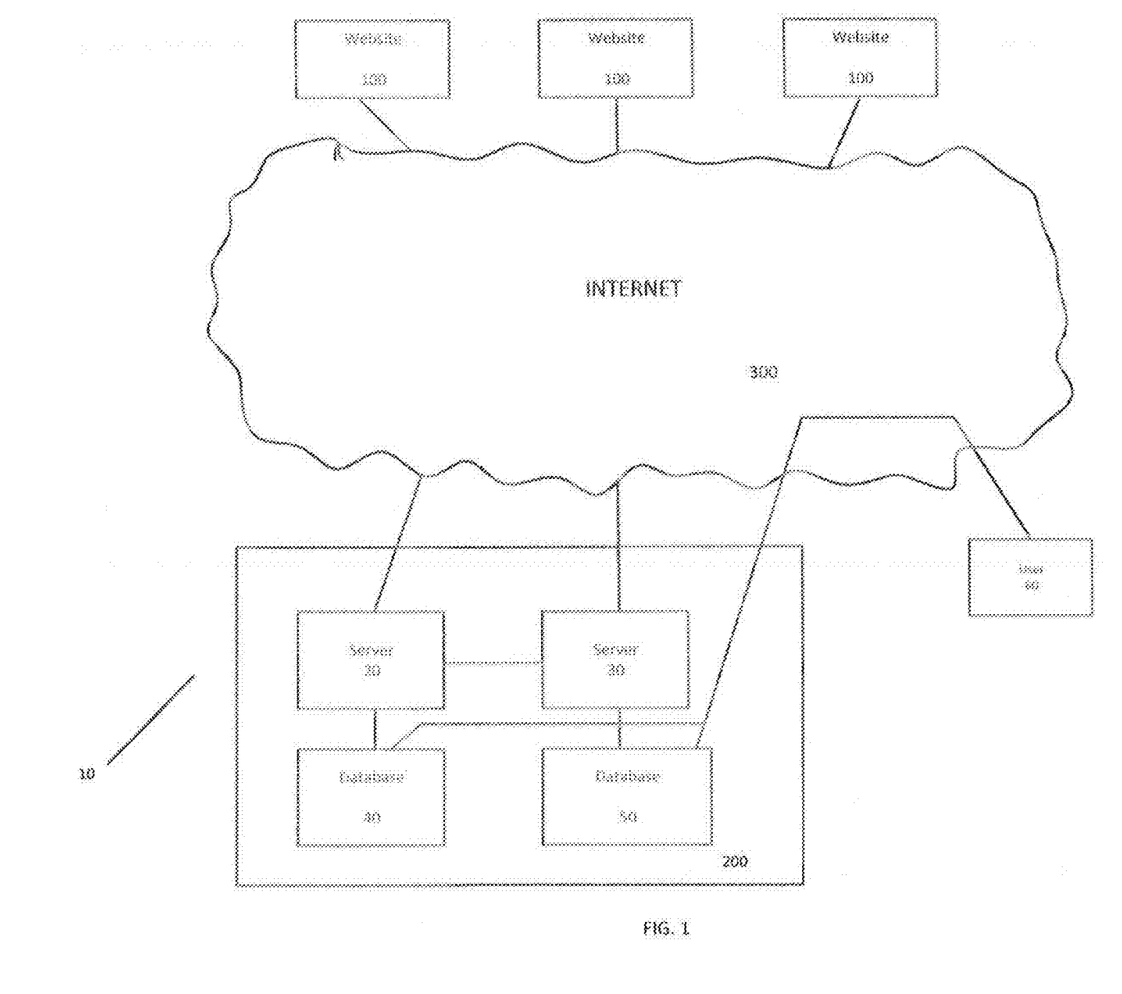
FIG. 1 is a block diagram showing an overview of an embodiment of a system according to the invention.

As shown in FIG. 1, system 10 includes first and second servers 20 and 30, and first and second databases 40 and 50. First server 20 is in communication with a plurality of healthcare policy websites 100 through a network, such as the Internet 300. First server 20 uses software to scan specified websites 100 having such healthcare policies, and communicates with first database 40 to determine if changes have occurred. Users 60 access first and second databases 40, 50 through a network, such as the Internet 300.

Figure 2:
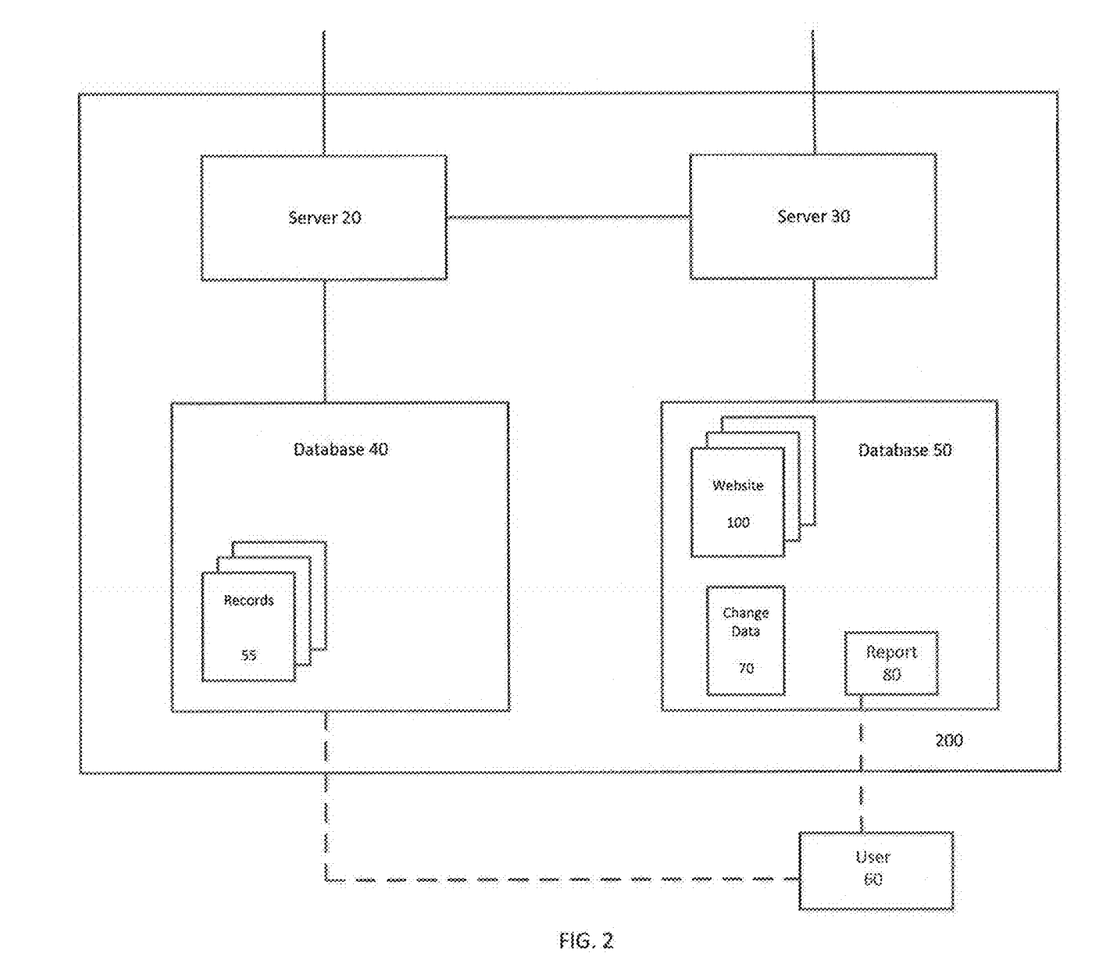
FIG. 2 is a block diagram showing the databases and servers in an embodiment of a system according to the invention.
Figure 3:
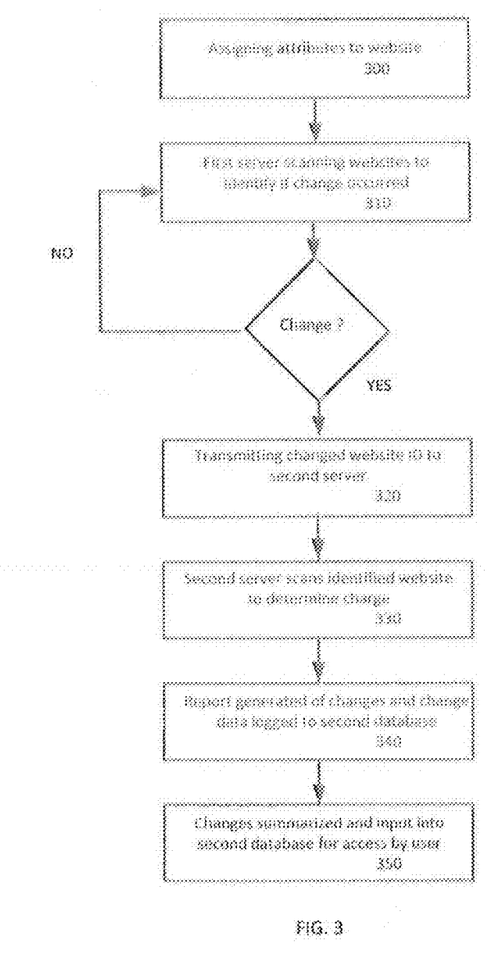
FIG. 3 is a flow chart showing the steps taken in an embodiment of a method according to the invention.

As shown in FIG. 2, database 40 contains records 55 of the text of each healthcare policy website 100 being tracked (websites 100 are selectable by user 60 to allow user 60 to determine which have changed). Records 55 may first be collected by server 20 and then copied and input into database 40 via the computer system 200 administrator backend. As shown in FIG. 3, in use of the system, specific attributes and serial ID fields are assigned to records 55 for each healthcare policy website 100 for future sorting and searching (step 300); some of these fields may include Title of Website, Disease State, Treatment Method, Drug Name, Formulary Name, Prior Authorization Form Name, Guideline Name, Immunization Schedule Name, Health Plan Name, and Name of Insurer. An administrator may specify features of each website 100 to increase readability of the underlying code to be scanned by the software script (e.g. by designating the website as an .html or .pdf file).

First server 20 then uses software to scan each website 100 identified in database 40 of websites 100 on a predetermined schedule (for example once or more per day depending on capacity) to determine if any changes to the text, code or document file size of the website has occurred by comparing the text at website 100 accessible on the Internet and being scanned to the most recent version of the text of the website stored in database 40 (step 310) in the appropriate record 55. Websites 100 with text that is identified as having been changed are recorded by serial ID and that information (i.e. that a change has occurred) is automatically transmitted to second server 30 (step 320). Websites 100 with text that has not changed are passed over and remain on the schedule to be reviewed again the next day, or the next timeslot if the scan occurs more than once a day.

Second server 30 receives the serial ID information of websites 100 that have changed and then downloads only those websites 100 to determine the exact nature of the change (step 330). Second server 30 downloads data and documents from healthcare policy websites in multiple formats including but not limited to HTML, XML, .PHP, .PDF, .DOC, JavaScript, AJAX, and .ASP, and records the data and text in database 50. Second server 30 then runs a server-side script to compare the existing data in the database with the newly downloaded data and generates a report to the administrator backend indicating the text that was added or removed from the document or file at the website 100, by serial ID (step 340). The differences in the text from the previous text stored in record 55 is referred to as change data.

Figure 6:
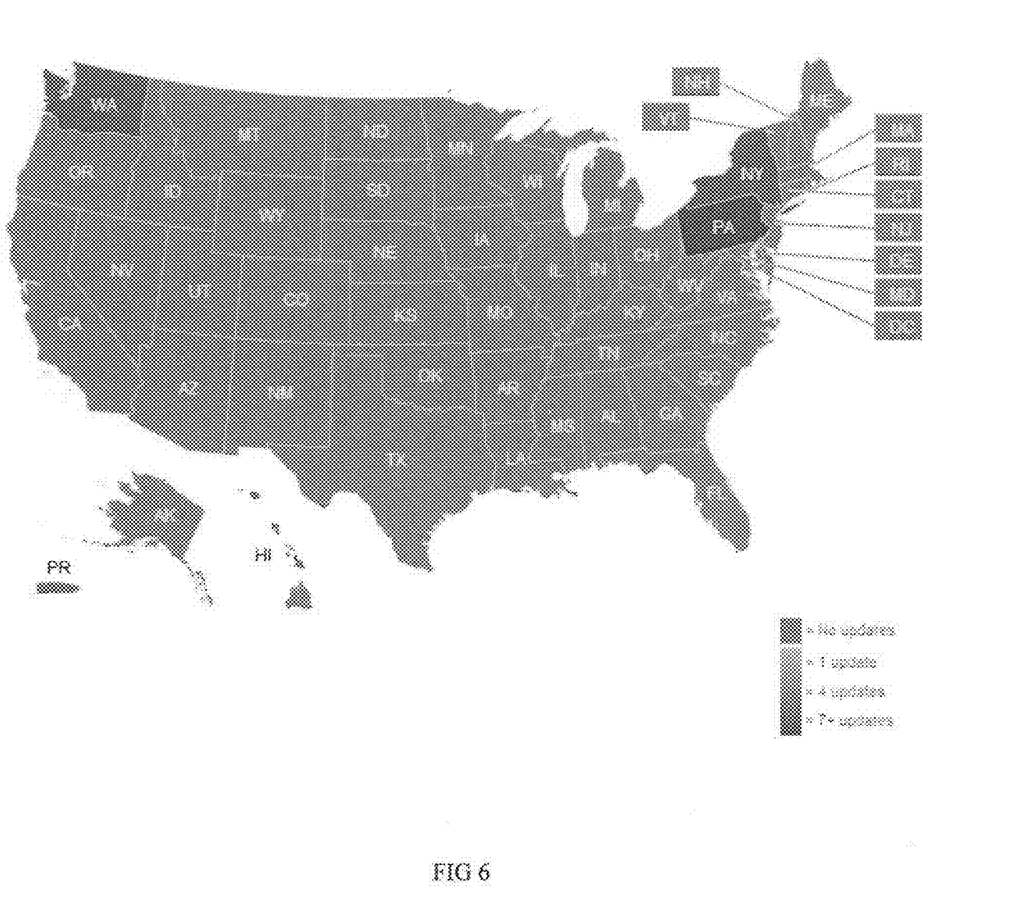
FIG. 6 shows an embodiment of a map displayable to users according to the invention.

The system scans and detects websites by URL, groups all websites that look identical, and labels them as "root" for the original website and "children" for all subsequent websites identical to the root. For all future scans, the system may scan only the root website, and attribute the result data to all the children websites to decrease server load. The system, through a script, automatically runs metrics on the quantity of changes attributed to a particular payer based on changes in the text from website 100, and then can display the information on a color coded graphical map, as shown in FIG. 6, which shows the concentration of changes of payer policies between various geographic regions.

Figure 4A:
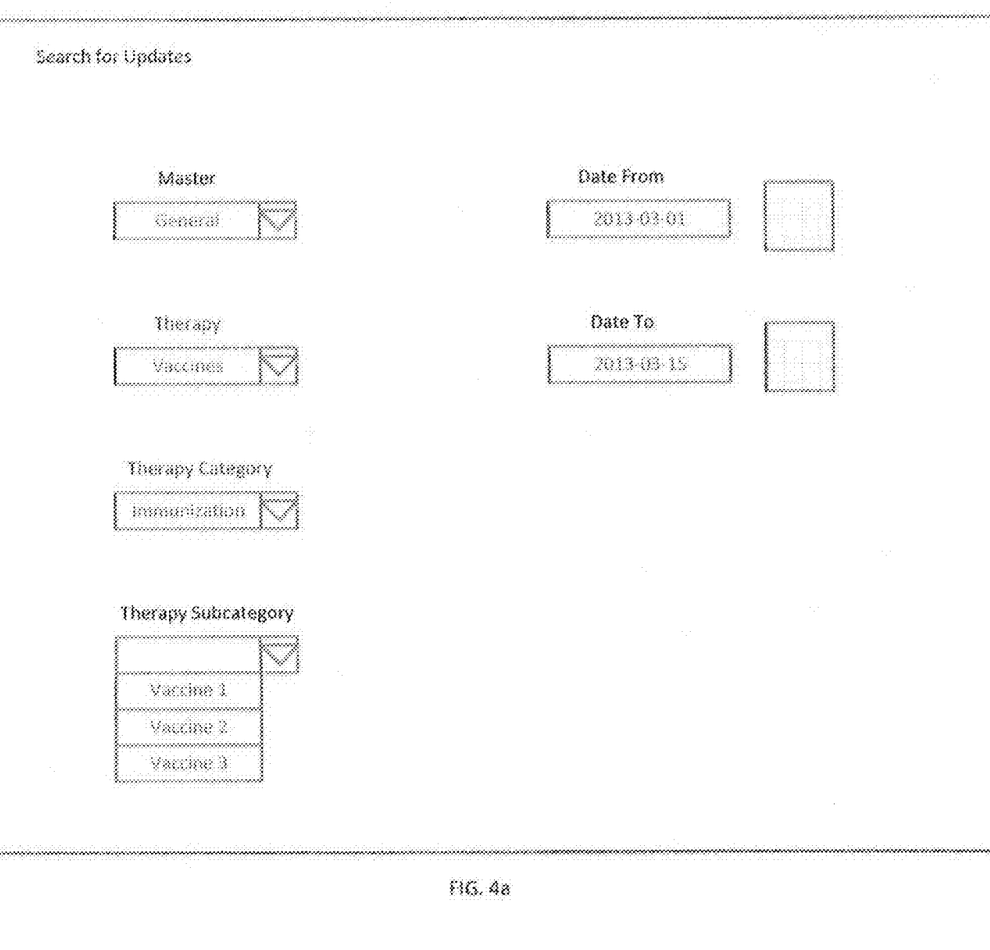
FIGS. 4a and 4b show an embodiment of a user interface according to the invention whereby a user can determine if changes have been made to a policy.
Figure 4B:
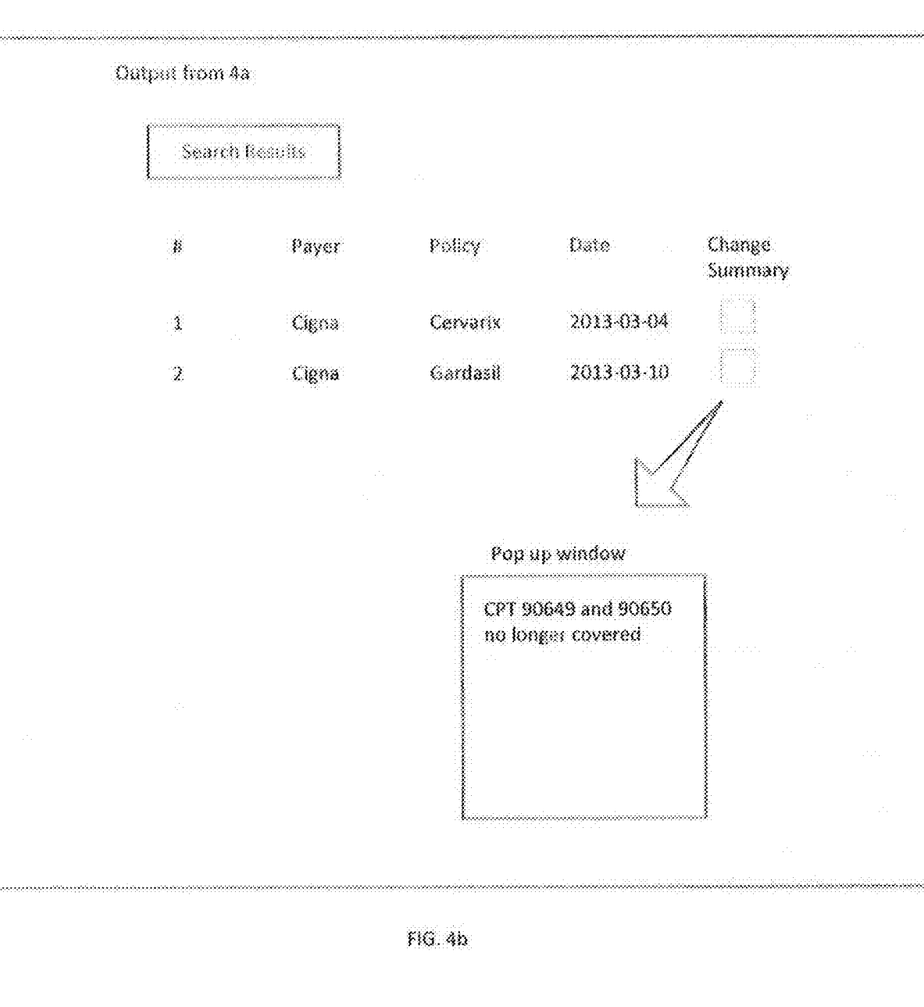

The change data 70 is automatically saved and logged into second database 50, and becomes searchable by a user on a number of fields, including the date the change occurred, and the attributes and fields originally designated for the specific document and/or website 100 input into first database 40. This information is searchable via a user interface accessible, as shown in FIG. 4a, by user 60 who can search change information by the specific attributes, as well as the data within the site in which the change occurred. The result of a query by the user 60 is shown in FIG. 4b. In the example shown a change to Gardisil policy has occurred and CPTs 90649 and 90650 are no longer covered, which is conveyed to the user in a pop up box displayed when the user clicks on, touches, scrolls over or otherwise indicates the change summary area.

The text that is added in the new version of the website 100 may be stored in a text file in one column, separated by line. The text that is removed in the previous version of website 100 stored in database 40 is stored in the same text file in a separate column, separated by line. Changes to text in a policy can be displayed to user 60 this way, or in a variety of other ways. In another embodiment, new text may be indicated with underlining and removed text shown as struck though.

The user may be notified through an automated system operated by one or both of first server 20 and second server 30 about changes to preselected websites. The system can send specific policy information contained in the databases via email, Short Message Service (SMS) or mobile application push notifications to the user. The change data, the insurer name and additional data elements may be contained within the message to user 60 and/or a link to the information can be included. Users may subscribe, via an administrative interface, to specific types and sub-types of messages and reports they would like to receive.

The newly updated website 100 is then analyzed and certain components of it may be summarized and ported to and saved at a second database 50, to be available for use as an analysis tool for the end user (step 350). Most insurer health policy websites 100 include common components for fields such as: Insurer Name; Website Name; Coverage Criteria; Prior Authorization; Previous and Next Review Dates; Coding; Background; Copay; Drug Tier Status; Preferred Pharmacy; Preferred Clinic; Preferred Physician Network; Health Plan; Coverage age range of patient; "Try and Fail" drug criteria; Conservative therapy criteria; clinical study lists; covered lives; and References. These fields may be autopopulated (for example using keywords), summarized, and input into corresponding fields of the administrative interface of the second database 50.

Figure 5A:
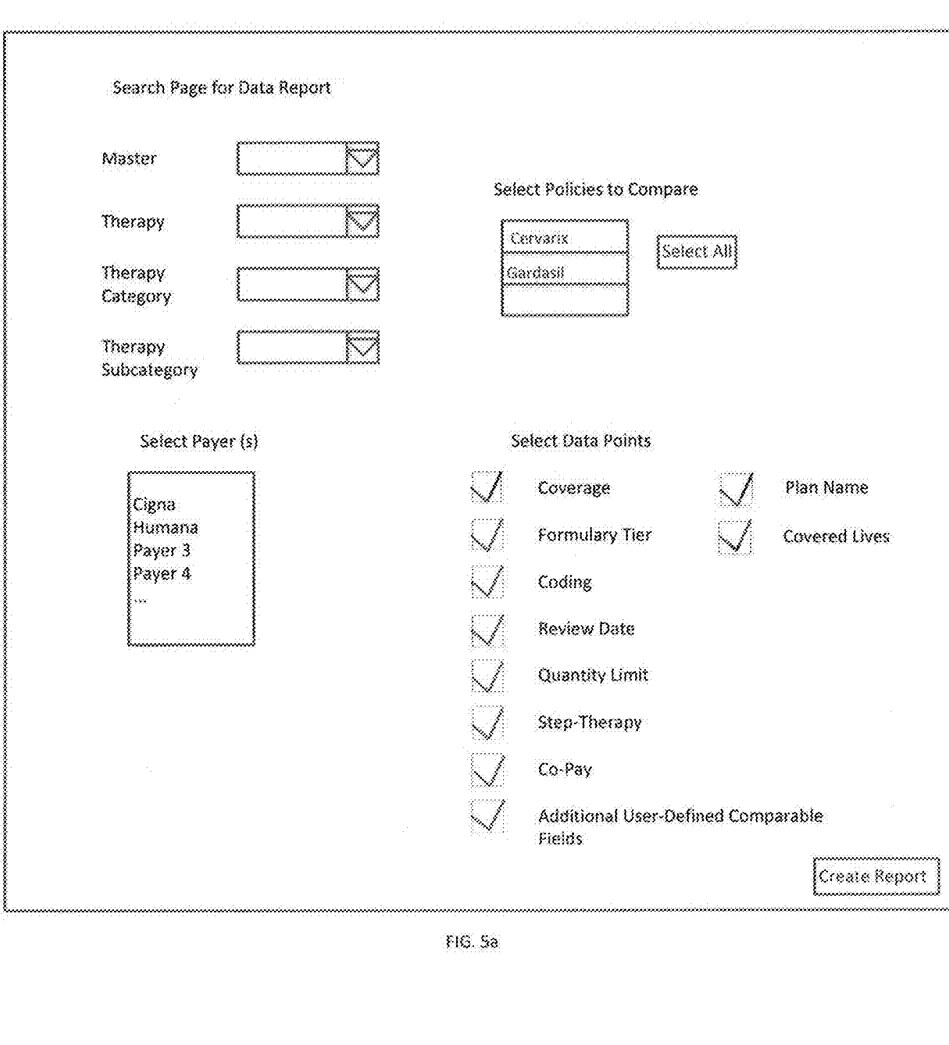
FIGS. 5a and 5b show an embodiment of a user interface according to the invention whereby a user can select data for display.
Figure 5B:
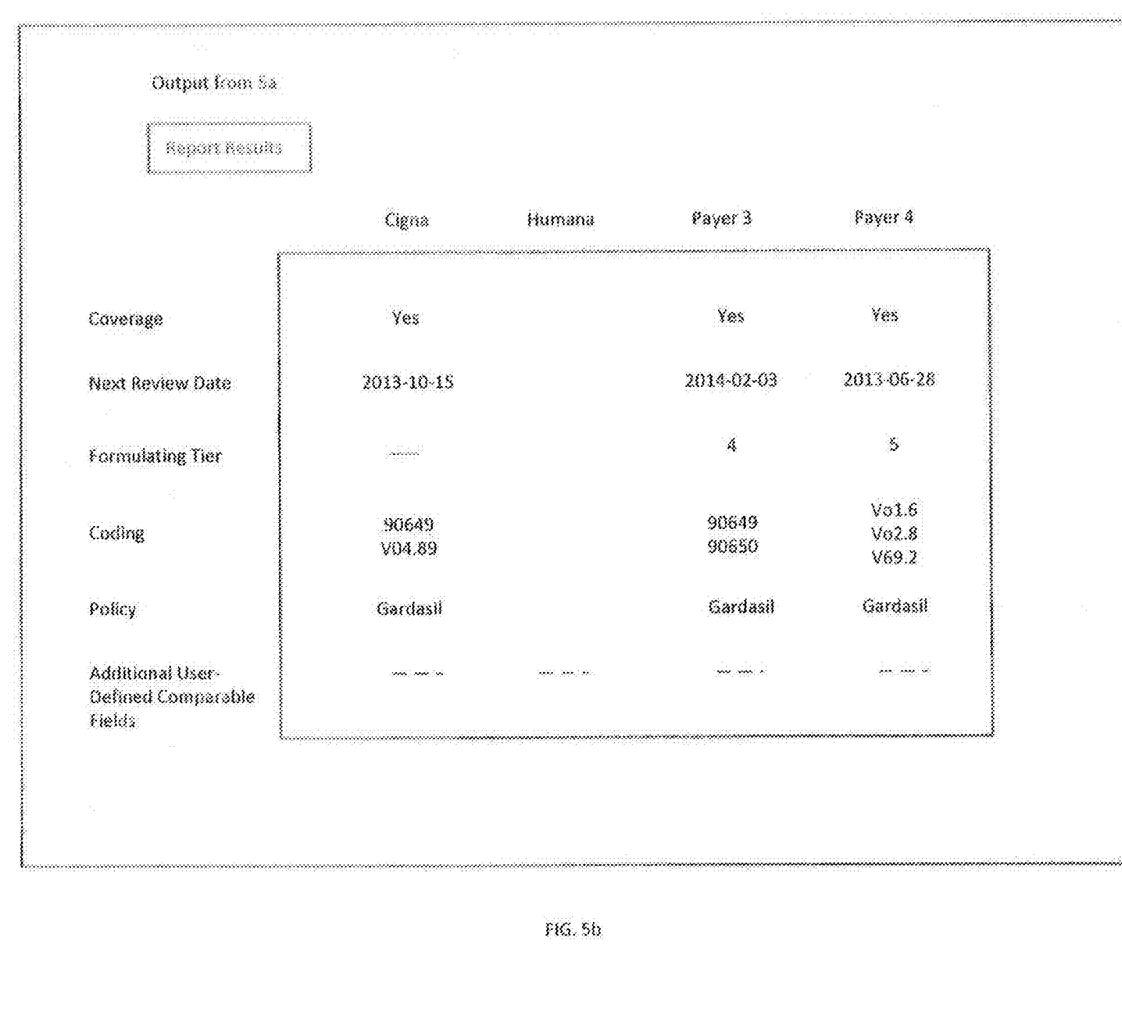

The user 60 can search database 50 by one or any of the aforementioned fields and select the insurer with which he or she wants to compare data, as shown in FIGS. 5a and 5b. For example, user 60, using the interface shown in FIG. 5a, may wish to compare coverage criteria and coding (or any combination of the inputted fields) for a number of insurers of their choosing (selectable from a dropdown menu). A report 80, an embodiment of which is shown in FIG. 5b, is then generated displaying the data, with the insurer names as column headings, and the selected fields as rows. Both headings and rows are sortable alphabetically and numerically. This table is then exportable into multiple file formats (.txt, .csv, .xlsx., .xls, .doc., .docx) for download by user 60.

A mobile application, accessible and executable on a mobile device, may connect to both databases and allow the user to access a separate mobile user interface. The mobile user interface allows the user to access the change data, search the website and document database and generate reports with optimized display, formatting and data output for various mobile devices, such as smart phones and tablets.

Figure 7:
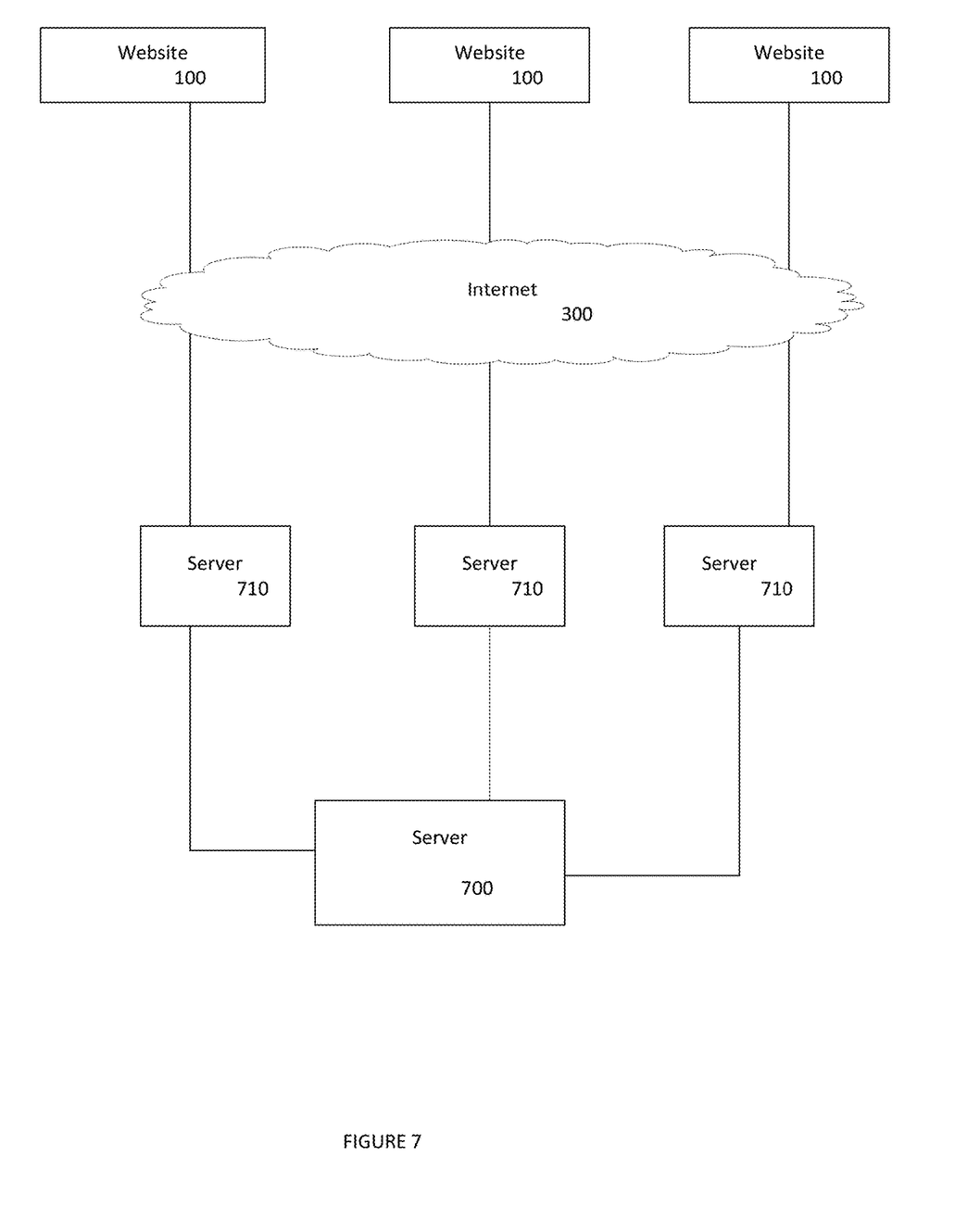
FIG. 7 is a block diagram of an alternative embodiment of the invention/
Figure 8:
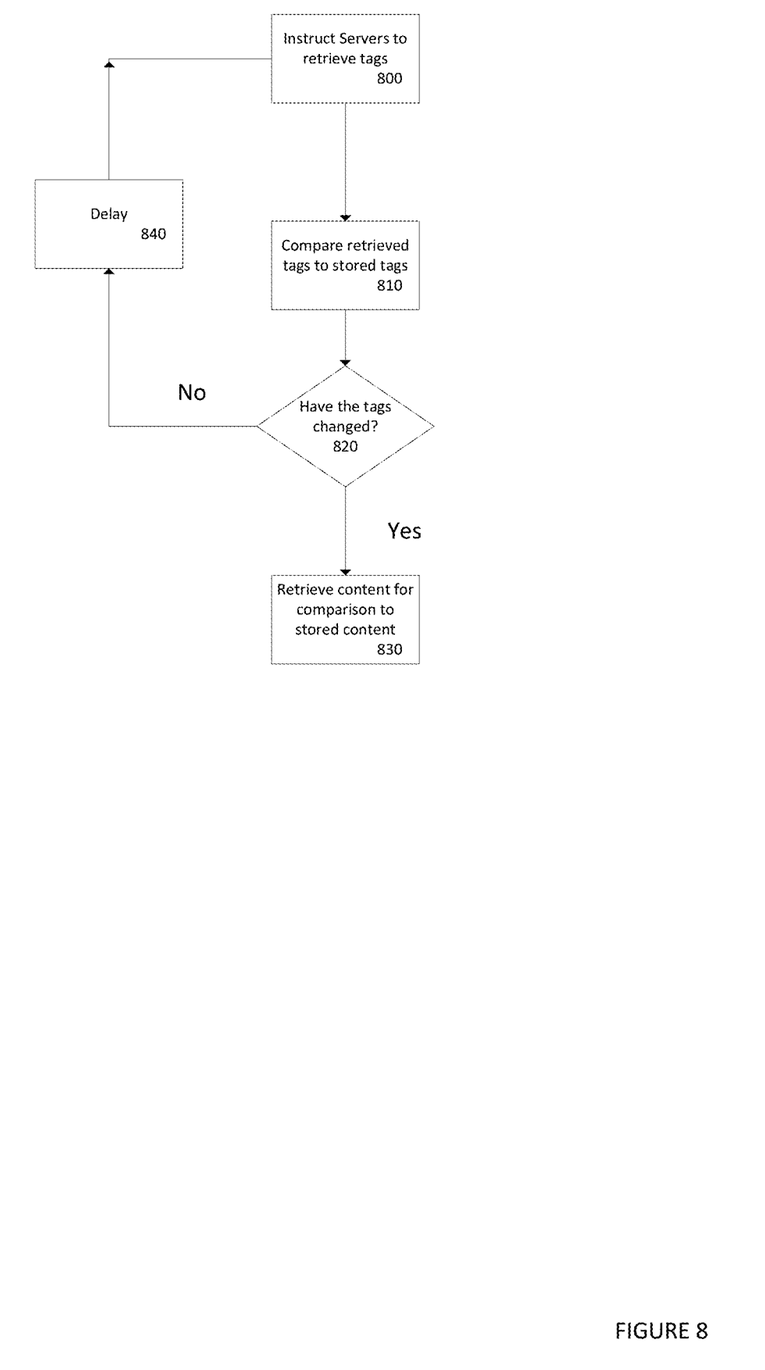
FIG. 8 is a flow chart of the alternative embodiment.

In an alternative embodiment of the invention, as shown in FIGS. 7 and 8, single server 700 can be used to detect changes to URLs associated with websites 100 related to healthcare policy information.

In this embodiment, server 700 send requests to one or more external servers 710 concurrently, instructing servers 710 to request the URLs simultaneously (step 800), rather than a single threaded request that is completed before the next one can start To reduce memory demands each server 710, rather than retrieving and transmitting the contents associated with the URL to server 700, retrieves specified tags associated with the URL which are sent to server 700 and stored. The next time these tags are retrieved server 710 compares the new tags to those previously stored (step 810). If there is a difference (step 820), the content of the corresponding URL will be downloaded and compared against previously downloaded content. Otherwise after a predetermined delay (step 840) the tags will be retrieved again. Examples of these tags include: Etag HTTP header, Last-modified tag, Content-type header, charset values, and md5 by checksum.

In the methods taught herein, the various acts may be performed in a different order than that illustrated and described. Additionally, the methods can omit some acts, and/or employ additional acts.

Changes can be made to the present systems, methods and articles in light of the above description. In general, in the following claims, the terms used should not be construed to limit the invention to the specific embodiments disclosed in the specification and the claims, but should be construed to include all possible embodiments along with the full scope of equivalents to which such claims are entitled. Accordingly, the invention is not limited by the disclosure, but instead its scope is to be determined entirely by the following claims.

Further and in addition to the disclosure provided above, it will be readily apparent to one of ordinary skill in the art that the various processes and methods described herein may be implemented by, e.g., appropriately programmed general purpose computers, special purpose computers and computing devices. Typically a processor (e.g., one or more microprocessors, one or more microcontrollers, one or more digital signal processors) will receive instructions (e.g., from a memory or like device), and execute those instructions, thereby performing one or more processes defined by those instructions. Instructions may be embodied in, e.g., a computer program.

A "processor" means one or more microprocessors, central processing units (CPUs), computing devices, microcontrollers, digital signal processors, or like devices or any combination thereof.

Thus a description of a process is likewise a description of an apparatus for performing the process. The apparatus that performs the process can include, e.g., a processor and those input devices and output devices that are appropriate to perform the process.

Further, programs that implement such methods (as well as other types of data) may be stored and transmitted using a variety of media (e.g., computer readable media) in a number of manners. In some embodiments, hard-wired circuitry or custom hardware may be used in place of, or in combination with, some or all of the software instructions that can implement the processes of various embodiments. Thus, various combinations of hardware and software may be used instead of software only.

The term "computer-readable medium" refers to any medium, a plurality of the same, or a combination of different media that participate in providing data (e.g., instructions, data structures) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

Various forms of computer readable media may be involved in carrying data (e.g. sequences of instructions) to a processor. For example, data may be (i) delivered from RAM to a processor; (ii) carried over a wireless transmission medium; (iii) formatted and/or transmitted according to numerous formats, standards or protocols, such as Ethernet (or IEEE 802.3), SAP, ATP, Bluetooth M., and TCP/IP, TDMA, CDMA, and 3G; and/or (iv) encrypted to ensure privacy or prevent fraud in any of a variety of ways well known in the art.

Thus a description of a process is likewise a description of a computer-readable medium storing a program for performing the process. The computer-readable medium can store (in any appropriate format) those program elements which are appropriate to perform the method.

Just as the description of various steps in a process does not indicate that all the described steps are required, embodiments of a system include a computer/computing device operable to perform some (but not necessarily all) of the described process.

Likewise, just as the description of various steps in a process does not indicate that all the described steps are required, embodiments of a computer-readable medium storing a program or data structure include a computer-readable medium storing a program that, when executed, can cause a processor to perform some (but not necessarily all) of the described process.

Where databases are described, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models and/or distributed databases) could be used to store and manipulate the data types described herein. Likewise, object methods or behaviors of a database can be used to implement various processes, such as the described herein. In addition, the databases may, in a known manner, be stored locally or remotely from a device which accesses data in such a database.

Various embodiments can be configured to work in a network environment including a computer that is in communication (e.g., via a communications network) with one or more devices. The computer may communicate with the devices directly or indirectly, via any wired or wireless medium (e.g. the Internet, LAN, WAN or Ethernet, Token Ring, a telephone line, a cable line, a radio channel, an optical communications line, commercial on-line service providers, bulletin board systems, a satellite communications link, a combination of any of the above). Each of the devices may themselves comprise computers or other computing devices, such as those based on the Intel® Pentium® or Centrino™ processor, that are adapted to communicate with the computer. Any number and type of devices may be in communication with the computer.

In an embodiment, a server computer or centralized authority may not be necessary or desirable. For example, the present invention may, in an embodiment, be practiced on one or more devices without a central authority. In such an embodiment, any functions described herein as performed by the server computer or data described as stored on the server computer may instead be performed by or stored on one or more such devices.

Where a process is described, in an embodiment the process may operate without any user intervention. In another embodiment, the process includes some human intervention (e.g., a step is performed by or with the assistance of a human).

As will be apparent to those skilled in the art, the various embodiments described above can be combined to provide further embodiments. Aspects of the present systems, methods and components can be modified, if necessary, to employ systems, methods, components and concepts to provide yet further embodiments of the invention. For example, the various methods described above may omit some acts, include other acts, and/or execute acts in a different order than set out in the illustrated embodiments.

The present methods, systems and articles also may be implemented as a computer program product that comprises a computer program mechanism embedded in a computer readable storage medium, which may be a non-transitory storage medium. For instance, the computer program product could contain program modules. These program modules may be stored on CD-ROM, DVD, magnetic disk storage product, flash media or any other computer readable data or program storage product. The software modules in the computer program product may also be distributed electronically, via the Internet or otherwise, by transmission of a data signal (in which the software modules are embedded) such as embodied in a carrier wave.

For instance, the foregoing detailed description has set forth various embodiments of the devices and/or processes via the use of examples. Insofar as such examples contain one or more functions and/or operations, it will be understood by those skilled in the art that each function and/or operation within such examples can be implemented, individually and/or collectively, by a wide range of hardware, software, firmware, or virtually any combination thereof. In one embodiment, the present subject matter may be implemented via ASICs. However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms taught herein are capable of being distributed as a program product in a variety of forms, and that an illustrative embodiment applies equally regardless of the particular type of signal bearing media used to actually carry out the distribution. Examples of signal bearing media include, but are not limited to, the following: recordable type media such as floppy disks, hard disk drives, CD ROMs, digital tape, flash drives and computer memory; and transmission type media such as digital and analog communication links using TDM or IP based communication links (e.g., packet links).

Although a few embodiments have been shown and described, it will be appreciated by those skilled in the art that various changes and modifications can be made to these embodiments without changing or departing from their scope, intent or functionality. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the claims that follow.

We claim:

1. A computer-implemented method of tracking changes in healthcare policy documents, using a computer system comprising a memory and a processor with access to the memory, the method comprising:

providing a first database stored by the memory, the first database containing a plurality of records, each record containing a copy of a website and tags associated with the website, the website from which original healthcare policy documents are located and downloaded into the first database, and wherein a field of each record in the first database includes at least one of the fields selected from the following: procedure name, medical device name, diagnostic test name, guideline name, vaccine name, drug name; name of insurer; and health plan name;

using the processor, retrieving current versions of tags associated with the websites on the Internet;

for each website, determining if the tags associated with the website have changed by comparing the current version of the tags to the copy of the tags in the first database;

if the tags have changed, updating the copy of the web site associated with the tags in the first database;

downloading updated healthcare policy documents from the website associated with the changed tags;

comparing the updated healthcare policy documents to the original healthcare policy documents in the first database to capture changes in the form of text that was added or removed from each of the updated healthcare policy documents;

providing a user device comprising a smartphone, a tablet, or a personal computer running an application connected to the first database;

allowing a user to search the first database and generate reports; and displaying, using the reports, a visualization of the changes to the text in the healthcare policy documents on the smartphone, the tablet, or the personal computer to the user.

2. The method of claim 1, wherein one or more servers to simultaneously retrieve the tags associated with the plurality of websites.

3. The method of claim 2 further comprising storing records including the changes made to each of the updated healthcare policy documents in a second database.

4. The method of claim 3 further comprising a first user interface, the first user interface configured to allow the user to search the first database.

5. The method of claim 4 wherein the second database is searchable by the user through a second user interface.

6. The method of claim 5, wherein a field of each record in the second database includes at least one of the fields selected from the following: procedure name, medical device name, diagnostic test name, guideline name, vaccine name, web site name; insurer name; and coverage criteria.

7. A non-transitory computer-readable medium carrying computer-executable instructions for tracking changes in healthcare policy documents, the instructions being executable by a processor to:

access a memory storing a first database, the first database containing a plurality of records, each record containing a copy of a web site and tags associated with the web site, the web site from which original healthcare policy documents are located and downloaded into the first database, and wherein a field of each record in the first database includes at least one of the fields selected from the following: procedure name, medical device name, diagnostic test name, guideline name, vaccine name, drug name; name of insurer; and health plan name;

request a plurality of servers to simultaneously retrieve current versions of tags associated with the websites on the Internet;

for each website, determine if the tags associated with the website have changed by comparing the current version of the tags to the copy of the tags in the first database; and if the tags have changed, update the copy of the website associated with the tags in the first database;

download updated healthcare policy documents from the website associated with the changed tags;

compare the updated healthcare policy documents to the original healthcare policy documents in the first database to capture changes in the form of text that was added or removed from each of the updated healthcare policy documents; and allow a user to search the first database and generate reports; and displaying, using the reports, a visualization of the changes to the text in the healthcare policy documents on the smartphone, the tablet, or the personal computer to the user.

* * * * *